US011760383B2

(12) United States Patent
Hara et al.

(10) Patent No.: US 11,760,383 B2
(45) Date of Patent: Sep. 19, 2023

(54) INFORMATION PROCESSING APPARATUS, INFORMATION PROCESSING SYSTEM, STORAGE MEDIUM, AND INFORMATION PROCESSING METHOD

(71) Applicant: TOYOTA JIDOSHA KABUSHIKI KAISHA, Toyota (JP)

(72) Inventors: Yusuke Hara, Musashino (JP); Shuhei Aketa, Koto-ku (JP); Toru Yanagida, Nagoya (JP); Shin Sakurada, Toyota (JP); Tae Sugimura, Miyoshi (JP); Yasutaka Ujihara, Meguro-ku (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 530 days.

(21) Appl. No.: 17/010,152

(22) Filed: Sep. 2, 2020

(65) Prior Publication Data

US 2021/0061314 A1 Mar. 4, 2021

(30) Foreign Application Priority Data

Sep. 2, 2019 (JP) .................... 2019-159914

(51) Int. Cl.
*B60W 60/00* (2020.01)
*G16H 20/10* (2018.01)
(Continued)

(52) U.S. Cl.
CPC ... *B60W 60/00256* (2020.02); *G01C 21/3407* (2013.01); *G01C 21/3438* (2013.01); *G01C 21/3484* (2013.01); *G06Q 10/047* (2013.01); *G06Q 10/06315* (2013.01); *G06Q 30/0631* (2013.01); *G08G 1/143* (2013.01); *G16H 10/20* (2018.01); *G16H 10/60* (2018.01); *G16H 20/10* (2018.01); *G16H 40/20* (2018.01); *G16H 50/70* (2018.01); *H04L 63/0876* (2013.01)

(58) Field of Classification Search
CPC ............ G01C 21/3407; G01C 21/3438; G01C 21/3484; G06Q 10/06315; G08G 1/143; G16H 10/60; G16H 10/10; G16H 10/70; H04L 63/0876; B60P 3/007
USPC ........................................................ 701/517
See application file for complete search history.

(56) References Cited

U.S. PATENT DOCUMENTS 11,530,929 B1 * 12/2022 Smith .................. G01C 21/343
2003/0125963 A1 * 7/2003 Haken .............. G06Q 10/08355
705/26.1
(Continued)

FOREIGN PATENT DOCUMENTS

JP 2002-321828 A 11/2002
JP 2017-204243 A 11/2017
(Continued)

*Primary Examiner* — Krishnan Ramesh
(74) *Attorney, Agent, or Firm* — Oliff PLC

(57) ABSTRACT

The present disclosure enables a reduction in the effort necessary for patients to receive pharmaceutical products. An information processing apparatus includes a controller. When prescription-related information is received, the controller sends, to an on-board apparatus for a vendor vehicle covering a moving area that includes at least part of a travel route along which a patient is expected to travel or a first terminal apparatus associated with a supplier that manages the vendor vehicle, at least one location on the travel route.

16 Claims, 2 Drawing Sheets

(51) Int. Cl.
*G16H 10/60* (2018.01)
*G16H 40/20* (2018.01)
*G06Q 10/047* (2023.01)
*G16H 50/70* (2018.01)
*G01C 21/34* (2006.01)
*G16H 10/20* (2018.01)
*G06Q 10/0631* (2023.01)
*H04L 9/40* (2022.01)
*G08G 1/14* (2006.01)
*G06Q 30/0601* (2023.01)

(56) References Cited

U.S. PATENT DOCUMENTS

| | | | |
|---|---|---|---|
| 2013/0090844 A1* | 4/2013 | Rakshit | G01C 21/20 |
| | | | 701/410 |
| 2015/0323330 A1* | 11/2015 | Lord | G06Q 10/025 |
| | | | 701/410 |
| 2017/0147929 A1* | 5/2017 | Tsunoda | G06Q 10/08355 |
| 2019/0047515 A1* | 2/2019 | Ferguson | B60R 25/25 |
| 2019/0066041 A1* | 2/2019 | Hance | G01C 21/3407 |
| 2019/0244522 A1* | 8/2019 | Makita | G06Q 10/02 |
| 2020/0209865 A1* | 7/2020 | Jarvis | B66F 9/063 |

FOREIGN PATENT DOCUMENTS

| | | |
|---|---|---|
| JP | 2019-502215 A | 1/2019 |
| WO | 2017/083517 A1 | 5/2017 |

\* cited by examiner

INFORMATION PROCESSING APPARATUS, INFORMATION PROCESSING SYSTEM, STORAGE MEDIUM, AND INFORMATION PROCESSING METHOD

CROSS-REFERENCE TO RELATED APPLICATION

The present application claims priority to Japanese Patent Application No. 2019-159914 filed on Sep. 2, 2019, the entire disclosure of which is incorporated herein by reference.

TECHNICAL FIELD

The present disclosure relates to an information processing apparatus, an information processing system, a storage medium, and an information processing method.

BACKGROUND

Pharmaceutical products need to be appropriately managed because they have relatively strong effects. For example, a medicine information sharing system has been developed in which a terminal apparatus installed at a medical facility obtains prescription data input to a terminal apparatus installed at a pharmacy, so that an in-clinic pharmacist at the medical facility can check information about medicines brought by a patient who is to stay in the medical facility (refer to PTL1).

CITATION LIST

Patent Literature

PTL 1: JP 2017-204243 A

SUMMARY

Pharmaceutical products need to be examined and prepared by pharmacists based on prescriptions. Hence, patients need to take prescriptions directly to pharmacies and wait for preparation of medicines.

An object of the present disclosure in consideration of the circumstances described above is to reduce the effort required by patients to receive the pharmaceutical products.

An information processing apparatus according to an embodiment of the present disclosure includes a controller configured to send, to an on-board apparatus for a vendor vehicle covering a moving area that includes at least part of a travel route along which a patient is expected to travel or a first terminal apparatus associated with a supplier that manages the vendor vehicle, at least one location on the travel route when prescription-related information on the patient is received.

An information processing system according to an embodiment of the present disclosure includes an information processing apparatus, an on-board apparatus for a vendor vehicle, and a first terminal apparatus. The information processing apparatus includes a controller configured to send, to the on-board apparatus for the vendor vehicle covering a moving area that includes at least part of a travel route along which a patient is expected to travel or a first terminal apparatus associated with a supplier that manages the vendor vehicle, at least one location on the travel route when prescription-related information on the patient is received. The on-board apparatus for the vendor vehicle is configured to communicate with the information processing apparatus. The first terminal apparatus is configured to communicate with the information processing apparatus.

A non-transitory computer-readable storage medium according to an embodiment of the present disclosure stores a program causing a first terminal apparatus to execute a process. The process includes receiving from an information processing apparatus a travel route along which a patient is expected to travel, determining, based on the travel route, a parking position at which a vendor vehicle covering a moving area that includes at least part of the travel route is to be parked, and sending the parking position to an on-board apparatus for the vendor vehicle.

An information processing method according to an embodiment of the present disclosure is implemented by an information processing apparatus. The information processing method includes receiving prescription-related information on a patient and sending, to an on-board apparatus for a vendor vehicle covering a moving area that includes at least part of a travel route along which the patient is expected to travel or a first terminal apparatus associated with a supplier that manages the vendor vehicle, at least one location on the travel route.

The information processing apparatus, the information processing system, the storage medium, and the information processing method according to an embodiment of the present disclosure can reduce the effort required by patients to receive pharmaceutical products.

BRIEF DESCRIPTION OF THE DRAWINGS

In the accompanying drawings.

DETAILED DESCRIPTION

Hereinafter, an embodiment of the present disclosure will be described with reference to the drawings.

Figure 1:
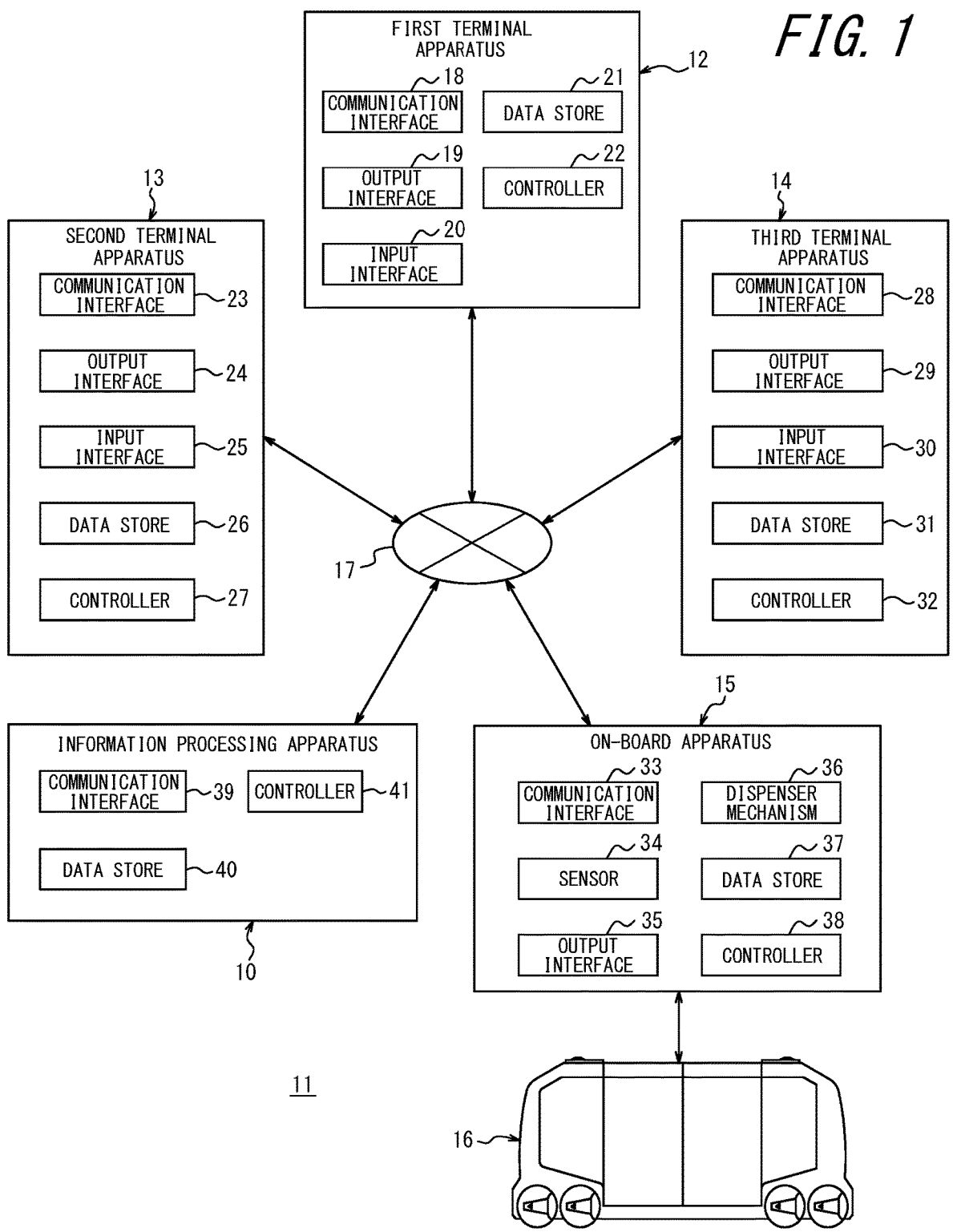
FIG. 1 is a configuration diagram illustrating an overall configuration of an information processing system including an information processing apparatus according to an embodiment of the present disclosure.

An information processing system 11 including an information processing apparatus 10 according to an embodiment of the present disclosure will be outlined with reference to FIG. 1. The information processing system 11 includes a first terminal apparatus 12, a second terminal apparatus 13, a third terminal apparatus 14, an on-board apparatus (an on-board apparatus for a vendor vehicle) 15, and the information processing apparatus 10.

The first terminal apparatus 12, the second terminal apparatus 13, and the third terminal apparatus 14 each are, for example, a general electronic device such as a smartphone or a personal computer (PC), but the first terminal apparatus 12, the second terminal apparatus 13, and the third terminal apparatus 14 are not limited to this example and each may be an electronic device dedicated to the information processing system 11. The first terminal apparatus 12 is installed at, for example, a business place of a supplier of pharmaceutical products such as a dispensing pharmacy. The second terminal apparatus 13 is owned by, for example, a patient. The third terminal apparatus 14 is installed at, for example, a medical facility. The on-board apparatus 15 is installed in a vendor vehicle 16. For example, the vendor vehicle 16 may be an autonomous vehicle that can perform automated driving or adaptive cruise control, but is not limited to these and may be any vehicle in which the on-board apparatus 15 can be installed. The information processing apparatus 10 includes one server apparatus or a plurality of server apparatuses that are capable of communicating with each other. While FIG. 1 illustrates one first terminal apparatus 12, one second terminal apparatus 13, one third terminal apparatus 14, and one on-board apparatus 15 for ease of description, the information processing system 11 only has to include at least one first terminal apparatus 12, at least one second terminal apparatus 13, at least one third terminal apparatus 14, and at least one on-board apparatus 15.

The first terminal apparatus 12, the second terminal apparatus 13, the third terminal apparatus 14, the on-board apparatus 15, and the information processing apparatus 10 are communicably connected to a network 17 which includes, for example, a mobile communication network and the Internet. At least part of the information processing system 11 is used for providing a mobility service (Mobility-as-a-Service: MaaS). Service providers can provide mobility services such as ridesharing services, mobile hotels, and mobile retail shops by using the on-board apparatus 15 and the vendor vehicle 16.

The outline of the present embodiment will be further explained. At a medical facility equipped with the third terminal apparatus 14, health care professionals provide medical services for patients. The third terminal apparatus 14 generates prescription-related information based on user inputs about prescriptions based on the medical services. It should be noted that, as used herein, "generate" denotes generating information on a target such as prescription-related information. When a patient desires to collect a pharmaceutical product by using the vendor vehicle 16, the prescription-related information is sent, directly or via the second terminal apparatus 13, to the information processing apparatus 10. It should be noted that, as used herein, "send" denotes sending information on a target such as prescription-related information. When the information processing apparatus 10 receives the prescription-related information, the information processing apparatus 10 recognizes, based on the prescription-related information as described later, a travel route along which a patient who is prescribed the prescription-related information is to travel. It should be noted that, as used herein, "receive" denotes receiving information on a target such as prescription-related information. The information processing apparatus 10 sends, to the on-board apparatus 15 installed in the vendor vehicle 16 covering a moving area including at least part of the travel route, at least one location on the travel route. Alternatively, the information processing apparatus 10 sends the location to the first terminal apparatus 12 associated with a supplier who manages the vendor vehicle 16. When the on-board apparatus 15 receives at least one location on the travel route, directly or indirectly via the first terminal apparatus 12, from the information processing apparatus 10, the vendor vehicle 16 equipped with the on-board apparatus 15 travels to reach any location on the travel route within a travel time period.

Next, the constituents of the information processing system 11 are described in detail.

The first terminal apparatus 12 includes a communication interface 18, an output interface 19, an input interface 20, a data store 21, and a controller 22.

The communication interface 18 includes a communication module that establishes connection with at least one of the network 17 and the other apparatuses constituting the information processing system 11. For example, the communication interface 18 may include a communication module compliant with mobile communication standards such as the Fourth Generation (4G) and the Fifth Generation (5G) standards. For example, the communication interface 18 may include a communication module compliant with a short-distance wireless communication standard such as Bluetooth® (Bluetooth is a registered trademark in Japan, other countries, or both). In the present embodiment, the first terminal apparatus 12 is connected to the network 17 via the communication interface 18. The communication interface 18 sends and receives various kinds of information through the network 17. When the communication interface 18 sends information through the network 17, the communication interface 18 may add identification information for the first terminal apparatus 12 to the information. The identification information for the first terminal apparatus 12 is information that can be used to uniquely identify the first terminal apparatus 12 in the information processing system 11.

The output interface 19 includes at least one interface that outputs information to notify users. For example, the output interface 19 may be, but is not limited to, a display that outputs information as an image or a speaker that outputs information in sound.

The input interface 20 includes at least one interface that detects user inputs. For example, the input interface 20 may be, but is not limited to, physical keys, capacitive keys, a touch screen provided in combination with a display of the output interface 19, a microphone that accepts sound input, or a camera that images an object.

The data store 21 may be, but is not limited to, a semiconductor memory, a magnetic memory, an optical memory, or the like. The data store 21 may function as, for example, a primary storage unit, an auxiliary storage unit, or a cache memory. The data store 21 stores any information that is used for operation of the first terminal apparatus 12. The data store 21 may store, for example, a system program and/or an application program.

The data store 21 may store a moving area of the vendor vehicle 16 managed by a supplier. It should be noted that, as used herein "store" denotes storing information on a target such as a moving area. The data store 21 may store an inventory of medicines of the individual business place of the supplier and an inventory of medicines of the individual vendor vehicle 16 managed by the supplier. The information stored in the data store 21 may be updated by using, for example, information received from the network 17 via the communication interface 18.

The controller 22 includes at least one processor. In the present embodiment, a "processor" may be, but is not limited to, a general processor or a processor dedicated to a particular processing operation. The dedicated processor may include an application-specific integrated circuit (ASIC). The controller 22 may include a programmable logic device (PLD). The PLD may include a field-programmable gate array (FPGA). The controller 22 controls the entire operation of the first terminal apparatus 12.

For example, when the input interface 20 detects a user input from the vendor vehicle 16 for requesting registration as a mobile retail service provider, the controller 22 generates registration information including the moving area of the vendor vehicle 16 and a location of the business place. It should be noted that, as used herein, "include" denotes including information on a target such as a moving area. The moving area is an area within which the service of selling medicines is provided by using the vendor vehicle 16. The moving area is freely set in accordance with user inputs by a corresponding supplier. The moving area may be previously recognized in accordance with a user input and stored in the data store 21 or may be recognized in accordance with a user input together with the request for registration. The controller 22 controls the communication interface 18 to send the registration information to the information processing apparatus 10.

When a replenishment quantity and a sales quantity of a kind of medicine are obtained, the controller 22 may update the inventory of medicines stored in the data store 21. It should be noted that, as used herein, "obtain" denotes obtaining information on a target such as a quantity. The controller 22 can obtain the quantity by detecting a user input of the quantity using the input interface 20 or by receiving the quantity via the communication interface 18.

More specifically, when the business place or the vendor vehicle 16 replenishes and sells medicines, the controller 22 may obtain replenishment quantities and sales quantities in accordance with user inputs by a salesperson. Alternatively, when the business place replenishes and sells medicines, the controller 22 may obtain replenishment quantities and sales quantities in accordance with user inputs entered by imaging a code such as a bar code on a surface of each medicine. Alternatively, to be more specific, when the medicines are replenished and sold in the vendor vehicle 16, the controller 22 may receive replenishment quantities and sales quantities, directly or via the information processing apparatus 10, from the on-board apparatus 15.

When changes occur in an inventory of medicines or when a request for an inventory report is received from the information processing apparatus 10, the controller 22 controls the communication interface 18 to send an updated inventory of medicines to the information processing apparatus 10.

When prescription-related information, which will be described later, is received from the information processing apparatus 10, the controller 22 stores the prescription-related information in the data store 21. It should be noted that the prescription-related information includes a prescription, or identification information for the third terminal apparatus 14 that generates a prescription and identification information for the prescription in the third terminal apparatus 14. The controller 22 causes the output interface 19 to output a prescription corresponding to the prescription-related information.

In a case in which the prescription-related information is a prescription, the controller 22 outputs the prescription. In a case in which the prescription-related information is the identification information for the third terminal apparatus 14 and identification information for a prescription, the controller 22 receives the identified prescription from the identified third terminal apparatus 14 through the network 17. The controller 22 then outputs the received prescription. In a case in which the prescription-related information includes the identification information for the third terminal apparatus 14 and identification information for a prescription, the controller 22 may receive a web page for the identified prescription from the identified third terminal apparatus 14 through the network 17. The controller 22 causes the prescription to be output by displaying the web page with a browser.

When the input interface 20 detects user input of a medicine name and a prescribed quantity that correspond to the output prescription, the controller 22 controls the communication interface 18 to send, together with the prescription-related information, the name and the prescribed quantity of the medicine to the information processing apparatus 10. In a case in which the prescription-related information is a prescription, the controller 22 deletes the prescription-related information from the data store 21.

When a prescribing cancellation indication is received from the information processing apparatus 10, the controller 22 deletes the prescription-related information stored in the data store 21.

When a travel route and a travel time period are received from the information processing apparatus 10, the controller 22 searches for allowable parking locations for the vendor vehicle 16 on the travel route. The controller 22 can search for allowable parking locations based on, for example, traffic signs at individual locations on the travel route, road information such as the number of lanes, and road condition in the travel time period. The controller 22 determines a location out of the discovered allowable parking locations as a parking location. After the parking location is determined, the controller 22 determines a collection time at which the vendor vehicle 16 is to reach the parking location and start waiting for arrival of a patient. The controller 22 calculates the collection time by, for example, calculating a time that a person usually takes to walk from a departure point of the travel route to the parking location and then adding the time to a start time point of the travel time period. The controller 22 controls the communication interface 18 to send the determined parking location and the determined collection time to the information processing apparatus 10.

When a dispensing completion indication is received from the information processing apparatus 10 or the on-board apparatus 15, the controller 22 terminates the prescription processing as described later. In a case in which the prescription itself is stored in the data store 21, the controller 22 terminates the prescription processing by attaching completion information to the prescription in a manner which prevents tampering. In a case in which the identification information for the third terminal apparatus 14 and identification information for the prescription are stored in the data store 21, the controller 22 controls the communication interface 18 to send a prescribing completion indication to the third terminal apparatus 14. In response to the prescribing completion indication, the controller 22 receives from the third terminal apparatus 14 the prescription to which completion information is attached in a manner which prevents tampering. The controller 22 terminates the prescription processing by storing the received prescription in the data store 21.

The second terminal apparatus 13 includes a communication interface 23, an output interface 24, an input interface 25, a data store 26, and a controller 27.

The specific configuration of the communication interface 23 is similar to the configuration of the communication interface 18 of the first terminal apparatus 12. In the present embodiment, the second terminal apparatus 13 is connected to the network 17 via the communication interface 23. Functions of the communication interface 23 are similar to the functions of the communication interface 18 of the first terminal apparatus 12. For example, when the communication interface 23 sends information through the network 17, the communication interface 23 may add identification information for the second terminal apparatus 13 to the information. The identification information for the second terminal apparatus 13 is information that can be used to uniquely identify the second terminal apparatus 13 in the information processing system 11.

The specific configuration and the functions of the output interface 24 are similar to the configuration and the functions of the output interface 19 of the first terminal apparatus 12.

The specific configuration and the functions of the input interface 25 are similar to the configuration and the functions of the input interface 20 of the first terminal apparatus 12.

The specific configuration and the functions of the data store 26 are similar to the configuration and the functions of the data store 21 of the first terminal apparatus 12. The data store 26 stores, for example, any information that is used for operation of the second terminal apparatus 13.

The specific configuration of the controller 27 is similar to the configuration of the controller 22 of the first terminal apparatus 12. The controller 27 controls the entire operation of the second terminal apparatus 13.

When prescription-related information is received from the third terminal apparatus 14, the controller 27 stores the prescription-related information in the data store 26. The controller 27 causes the output interface 24 to output a reception indication for the prescription-related information.

When the input interface 25 detects a user input to request viewing of the prescription, the controller 27 causes the output interface 24 to output the prescription by using the prescription-related information as described later. For example, in a case in which the prescription-related information is the prescription, the controller 27 outputs the prescription. For example, in a case in which the prescription-related information includes the identification information for the third terminal apparatus 14 and identification information for the prescription, the controller 27 receives the identified prescription from the identified third terminal apparatus 14 and outputs the prescription. For example, in a case in which the prescription-related information includes the identification information for the third terminal apparatus 14 and identification information for the prescription, the controller 27 may receive a web page for the identified prescription from the identified third terminal apparatus 14 and cause the prescription to be output by displaying the web page with a browser.

When the input interface 25 detects a user input to request collection of a medicine from the vendor vehicle 16, the controller 27 causes the output interface 24 to output a request for user input of a travel route and a travel time period. The controller 27 recognizes, in either a semiautomatic manner or a manual manner, user input of the travel route and the travel time period.

When the input interface 25 detects a user input selecting the semiautomatic manner, the controller 27 reads an activity history of an owner of the second terminal apparatus 13 from the data store 26. The activity history includes, for example, a record of a time and a location at which the second terminal apparatus 13 exists, a record of use of a particular function of a particular application, and the like. The location of the second terminal apparatus 13 can be detected by using a position sensor, such as a Global Positioning System (GPS) receiver.

Based on the activity history, the controller 27 estimates a route along which the owner is expected to travel. The controller 27 determines a departure point and a destination point of travel by the owner based on, for example, temporary locations at which the second terminal apparatus 13 temporarily exists, times at which the second terminal apparatus 13 exists at the temporary locations, frequencies of existence on an hourly basis, and a day of the week and a time at which a user input selecting the semiautomatic manner is entered, which are obtained based on the activity history. Based on the determined departure point and the determined destination point, the controller 27 generates a route expected to be traveled.

The controller 27 causes the output interface 24 to output the generated route as a route along which the owner is expected to travel. The controller 27 causes the output interface 24 to output a request for a user input indicating whether the output route can be approved. In a case in which the input interface 25 detects a user input indicating approval, the controller 27 recognizes the approved route as a travel route input by the user. In a case in which the input interface 25 detects a user input indicating denial of approval, the controller 27 repeats generation and output other routes until the user approves a particular route.

Additionally, the controller 27 estimates, based on the activity history, a time period in which the owner is expected to pass through the travel route. For example, the controller 27 estimates, based on the activity history, a time at which the owner is expected to exist at a temporary location that is the departure point or the destination point, and based on the estimated time, the controller 27 estimates a time period in which the owner is expected to pass through the travel route. The controller 27 causes the output interface 24 to output a request for a user input indicating whether the estimated time period can be approved. In a case in which the input interface 25 detects a user input indicating approval, the controller 27 recognizes the approved time period as a travel time period input by the user.

In a case in which the input interface 25 detects a user input indicating denial of approval, the controller 27 causes the output interface 24 to output a request for a user input for correcting the approved time period. In a case in which the input interface 25 detects a user input for correcting the approved time period, the controller 27 recognizes the corrected time period as a travel time period input by the user.

In a case in which the input interface 25 detects a user input for selecting the manual manner, the controller 27 causes the output interface 24 to output a request for user input of a departure point and a destination point, and when necessary, a stopover point. When the input interface 25 detects user input of a departure point and a destination point, the controller 27 recognizes a route connecting the departure point and the destination point as a travel route input by the user. When the input interface 25 additionally detects a user input of a stopover point, the controller 27 recognizes a route for traveling from the departure point via the stopover point and reaching the destination point as a travel route input by the user.

The controller 27 causes the output interface 24 to output a request for a user input of a travel time period in which the travel route is expected to be passed. The controller 27 recognizes, in accordance with a detection result by the input interface 25, a travel time period input by the user.

When the controller 27 recognizes user input of the travel route and the travel time period, the controller 27 sends prescription-related information together with the travel route and the travel time period to the information processing apparatus 10. In a case in which the prescription-related information is the prescription itself, the controller 27 deletes the prescription-related information from the data store 26.

Instead of receiving prescription-related information, recognizing a travel route and a travel time period, and sending prescription-related information to the information processing apparatus 10, which are described above, the controller 27 may request that the third terminal apparatus 14 send prescription-related information to the information processing apparatus 10. When the input interface 25 detects a user input requesting that the third terminal apparatus 14 send prescription-related information to the information processing apparatus 10, the controller 27 controls the communication interface 23 to send the request together with the identification information for the second terminal apparatus 13 to the third terminal apparatus 14. It should be noted that the request may be sent through short-distance wireless communication.

The controller 27 may additionally send, together with the prescription-related information, at least one of a purchase history, an activity history, a medical examination history, a medication history, and an allergy record, which are stored in the data store 26, to the information processing apparatus 10. The purchase history includes purchase records each containing a name, a type, and the like of an item stored in the data store 26, for example, in a case in which the second terminal apparatus 13 functions as a means for settling payments for items or the like. The medical examination history includes records which are stored in the data store 26 regarding medical examinations having been conducted with respect to illnesses of the owner of the second terminal apparatus 13 has suffered from. The medication history includes records which are stored in the data store 26 regarding medicines that the owner of the second terminal apparatus 13 has taken. The allergy record is information for identifying foods or the like that cause allergy symptoms in the owner of the second terminal apparatus 13.

When a parking location, a collection time, and authentication information are received from the information processing apparatus 10, the controller 27 stores the parking location, the collection time, and the authentication information in the data store 26. The controller 27 causes the output interface 24 to output the parking location of the vendor vehicle 16 at which medicines are handed over and a collection time at which medicines are handed over. Additionally, in a case in which an item suggestion is received from the information processing apparatus 10, the controller 27 may cause the output interface 24 to output the item suggestion.

When presentation of authentication information to the on-board apparatus 15 is requested, the controller 27 reads authentication information from the data store 26 and presents the authentication information to the on-board apparatus 15. Requesting presentation to the on-board apparatus 15 is performed by, for example, the input interface 25 detecting a user input. Alternatively, requesting presentation to the on-board apparatus 15 is performed by, for example, the communication interface 23 receiving a request from the on-board apparatus 15 through short-distance wireless communication. Presenting authentication information to the on-board apparatus 15 is performed by, for example, the output interface 24 outputting the authentication information. Alternatively, presenting authentication information to the on-board apparatus 15 is performed by, for example, sending the authentication information to the on-board apparatus 15 through short-distance wireless communication.

The third terminal apparatus 14 includes a communication interface 28, an output interface 29, an input interface 30, a data store 31, and a controller 32.

The specific configuration of the communication interface 28 is similar to the configuration of the communication interface 18 of the first terminal apparatus 12. In the present embodiment, the third terminal apparatus 14 is connected to the network 17 via the communication interface 28. Functions of the communication interface 28 are similar to the functions of the communication interface 18 of the first terminal apparatus 12. For example, when the communication interface 28 sends information through the network 17, the communication interface 28 may add identification information for the third terminal apparatus 14 to the information. The identification information for the third terminal apparatus 14 is information that can be used to uniquely identify the third terminal apparatus 14 in the information processing system 11.

The specific configuration and the functions of the output interface 29 are similar to the configuration and the functions of the output interface 19 of the first terminal apparatus 12.

The specific configuration and the functions of the input interface 30 are similar to the configuration and the functions of the input interface 20 of the first terminal apparatus 12.

The specific configuration and the functions of the data store 31 are similar to the configuration and the functions of the data store 21 of the first terminal apparatus 12. The data store 31 stores, for example, any information that is used for operation of the third terminal apparatus 14.

The specific configuration of the controller 32 is similar to the configuration of the controller 22 of the first terminal apparatus 12. The controller 32 controls the entire operation of the third terminal apparatus 14.

For example, when the input interface 30 detects a user input of a prescription from a doctor or the like, the controller 32 stores the prescription in the data store 31. Based on the prescription, the controller 32 generates prescription-related information. As described above, the prescription-related information includes the prescription, or the identification information for the third terminal apparatus 14 and identification information for the prescription. When the controller 32 generates identification information for a prescription as prescription-related information, the controller 32 may generate a web page for the prescription and store the web page in the data store 31. It should be noted that the controller 32 may cause a prescription to be printed and the actual printed prescription may be provided to a patient.

For example, after the prescription-related information is generated, when communication with the second terminal apparatus 13 can be established by using short-distance wireless communication, the controller 32 controls the communication interface 28 to send the prescription-related information to the second terminal apparatus 13.

Alternatively, for example, when a request to send prescription-related information to the information processing apparatus 10 is received from the second terminal apparatus 13, the controller 32 controls the communication interface 28 to send the prescription-related information, together with the identification information for the second terminal apparatus 13 received with the request, to the information processing apparatus 10.

When a request for a prescription is received from at least one of the first terminal apparatus 12, the second terminal apparatus 13, and the information processing apparatus 10, the controller 32 controls the communication interface 28 to send the prescription or a web page for the prescription. The controller 32 deletes the prescription from the data store 31 after the prescription is sent.

When a prescribing completion indication is received from the first terminal apparatus 12, the controller 32 reads a prescription from the data store 31 and attaches completion information to the prescription in a manner which prevents tampering. The controller 32 controls the communication interface 28 to send to the first terminal apparatus 12 the prescription to which the completion information is attached in a manner which prevents tampering. The controller 32 deletes the prescription from the data store 31 after the prescription is sent.

The on-board apparatus 15 is installed in the vendor vehicle 16 as described above. For example, the vendor vehicle 16 may be, but is not limited to, an autonomous vehicle that can perform automated driving or adaptive cruise control; the vendor vehicle 16 may be any vehicle in which the on-board apparatus 15 can be installed.

The on-board apparatus 15 automatically generates control information by using automatic driving control software, and sends the control information to the vendor vehicle 16. The vendor vehicle 16 performs vehicle control in accordance with the received control information. For example, the vehicle control may be, but is not limited to, automated driving control. At least part of an application programming interface (API) in which specifications for control information are defined is disclosed to service providers. Service providers can freely develop automatic driving control software for the on-board apparatus 15 by programming with the use of the disclosed API. Thus, the service providers can provide a mobility service by installing facilities according to a particular purpose in a space in the vehicle cabin of the vendor vehicle 16 and by developing automatic driving control software by programming with the use of the API in accordance with the purpose.

The on-board apparatus 15 includes a communication interface 33, a sensor 34, an output interface 35, a dispenser mechanism 36, a data store 37, and a controller 38.

The communication interface 33 includes a communication module that establishes communication through an in-vehicle network of the vendor vehicle 16, such as a controller area network (CAN), or a dedicated line in the vendor vehicle 16. The communication interface 33 may also include a communication module that establishes connection with the network 17. For example, the communication interface 33 may also include a communication module compliant with a short-distance wireless communication standard such as Bluetooth®. In the present embodiment, the on-board apparatus 15 is connected to on-board devices such as a control apparatus and a location information acquisition apparatus of the vendor vehicle 16 via the communication interface 33 and communicates information. The on-board apparatus 15 is also connected to the network 17 via the communication interface 33, or the communication interface 33 and a communication apparatus of the vendor vehicle 16. When the communication interface 33 sends information through the network 17, the communication interface 33 may add identification information for the on-board apparatus 15 to the information. The identification information for the on-board apparatus 15 is information that can be used to uniquely identify the on-board apparatus 15 in the information processing system 11.

The sensor 34 includes, for example, a banknote counter and a coin counter and detects the amount of money paid to the vendor vehicle 16. The sensor 34 includes an imaging sensor, such as a camera, and detects the quantity of a medicine loaded to the dispenser mechanism 36 and the quantity of a medicine dispensed from the dispenser mechanism 36.

The specific configuration and the functions of the output interface 35 are similar to the configuration and the functions of the output interface 19 of the first terminal apparatus 12.

The dispenser mechanism 36 includes a storage space in which medicines are stored separately by type and a transport path and an actuator that are used for transporting medicines in controlled quantities separately by type from the storage space. The dispenser mechanism 36 dispenses a particular quantity of a particular medicine to a patient based on the control of the controller 38. The storage space may store items other than medicines. When items other than medicines are stored, these items in controlled quantities may be transported separately by type by using the transport path and the actuator.

The specific configuration and the functions of the data store 37 are similar to the configuration and the functions of the data store 21 of the first terminal apparatus 12. The data store 37 stores, for example, any information that is used for operation of the on-board apparatus 15.

The specific configuration of the controller 38 is similar to the configuration of the controller 22 of the first terminal apparatus 12. The controller 38 controls the entire operation of the on-board apparatus 15.

When a request for notification of a location of the vendor vehicle 16 is received from the information processing apparatus 10, the controller 38 controls the communication interface 33 to send the location of the vendor vehicle 16 received from the location information acquisition apparatus to the information processing apparatus 10.

When a parking location, a collection time, a medicine name, a prescribed quantity, authentication information, and an item suggestion are received from the information processing apparatus 10, the controller 38 stores the parking location, the collection time, the medicine name, the prescribed quantity, the authentication information, and the item suggestion in the data store 37.

The controller 38 generates control information for controlling the vendor vehicle 16 to move to the parking location by the collection time. The controller 38 controls the communication interface 33 to send the generated control information to the control apparatus.

When authentication information is obtained from the second terminal apparatus 13 while the vendor vehicle 16 is parked, the controller 38 reads identical authentication information from the data store 37. It should be noted that the authentication information can be obtained such that the authentication information is received through short-distance wireless communication with the second terminal apparatus 13 or information output by the output interface 24 of the second terminal apparatus 13 is detected by the sensor 34. Based on a medicine name and a prescribed quantity received together with the read authentication information, the controller 38 causes the output interface 35 to output a price that the patient is charged.

When an item suggestion has been received together with a parking location and the like, in a case in which authentication information is received from the second terminal apparatus 13 through short-distance wireless communication, the controller 38 may cause the output interface 35 to output an item purchase suggestion based on the item suggestion.

The controller 38 controls the sensor 34 to detect the amount of money paid by the patient. When the amount of money paid is equal to or greater than the price, the controller 38 controls the dispenser mechanism 36 to dispense the medicine in the prescribed quantity to the patient.

After the medicine is dispensed to the patient, the controller 38 controls the communication interface 33 to send a dispensing completion indication, which indicates that dispensing has been completed, to the first terminal apparatus 12 or the information processing apparatus 10. After the medicine is dispensed to the patient, the controller 38 controls the communication interface 33 to send the dispensed sales quantity to the patient, directly or via the information processing apparatus 10, to the first terminal apparatus 12. It should be noted that, when a medicine is replenished for the vendor vehicle 16, the controller 38 controls the communication interface 33 to send a replenishment quantity, directly or via the information processing apparatus 10, to the first terminal apparatus 12.

The information processing apparatus 10 includes a communication interface 39, a data store 40, and a controller 41.

The specific configuration of the communication interface 39 is similar to the configuration of the communication interface 18 of the first terminal apparatus 12. In the present embodiment, the information processing apparatus 10 is connected to the network 17 via the communication interface 39. Functions of the communication interface 39 are similar to the functions of the communication interface 18 of the first terminal apparatus 12. For example, when the communication interface 39 sends information through the network 17, the communication interface 39 may add identification information for the information processing apparatus 10 to the information. The identification information for the information processing apparatus 10 is information that can be used to uniquely identify the information processing apparatus 10 in the information processing system 11.

The specific configuration and the functions of the data store 40 are similar to the configuration and the functions of the data store 21 of the first terminal apparatus 12. The data store 40 stores, for example, any information that is used for operation of the information processing apparatus 10.

The specific configuration of the controller 41 is similar to the configuration of the controller 22 of the first terminal apparatus 12. The controller 41 controls the entire operation of the information processing apparatus 10.

When registration information is received from the first terminal apparatus 12, the controller 41 stores, in the data store 40, the moving area of the vendor vehicle 16 and the location of the business place, which are included in the registration information, in association with the identification information for the first terminal apparatus 12.

When an inventory of medicines of the business place and an inventory of medicines of the vendor vehicle 16 are received from the first terminal apparatus 12, the controller 41 updates an inventory stored in the data store 40 in association with the identification information for the first terminal apparatus 12. The controller 41 may control the communication interface 39 to periodically or regularly send a request for an inventory report to the first terminal apparatus 12 as described above. The controller 41 may receive the inventory of medicines for the vendor vehicle 16 from the on-board apparatus 15 and update the inventory.

When prescription-related information, a travel route, a travel time period, and at least one of a purchase history, an activity history, a medical examination history, a medication history, and an allergy record are received from the second terminal apparatus 13, the controller 41 stores the received information in the data store 40 in association with the identification information for the second terminal apparatus 13.

When prescription-related information and the identification information for the second terminal apparatus 13 are received from the third terminal apparatus 14, the controller 41 stores the received information in the data store 40 in association with the identification information for the second terminal apparatus 13. Based on the identification information for the second terminal apparatus 13, the controller 41 recognizes a travel route and a travel time period in which the owner of the second terminal apparatus 13 is expected to travel. The controller 41 may receive the travel route and the travel time period by, for example, submitting a request to send the travel route to the second terminal apparatus 13 or a server apparatus or the like that monitors the activity history of the second terminal apparatus 13.

Alternatively, for example, the controller 41 may submit a request to send an activity history to the second terminal apparatus 13 or a server apparatus or the like that manages the activity history and the like of the second terminal apparatus 13, receive the activity history, and estimate the travel route and the travel time period based on the activity history. Alternatively, for example, the controller 41 may read, based on the identification information for the second terminal apparatus 13, the activity history of the second terminal apparatus 13 collected in the data store 40 and estimate the travel route and the travel time period. The controller 41 stores, in the data store 40, the recognized travel route and the recognized travel time period in association with the identification information for the second terminal apparatus 13. Additionally, based on the identification information for the second terminal apparatus 13, the controller 41 may receive a purchase history, an activity history, a medical examination history, a medication history, and an allergy record from the second terminal apparatus 13 or the server apparatus or the like that monitors the activity history and the like of the second terminal apparatus 13.

The controller 41 reads, from the data store 40, the identification information for the first terminal apparatus 12 associated with the vendor vehicle 16 covering a moving area including at least part of a travel route stored in the data store 40. The controller 41 controls the communication interface 39 to send prescription-related information to the first terminal apparatus 12 corresponding to the read identification information. In a case in which the prescription-related information is a prescription, the controller 41 deletes the prescription-related information from the data store 21.

It is assumed that the controller 41 recognizes a medicine name and a prescribed quantity that correspond to the prescription-related information by receiving the medicine name and the prescribed quantity from the first terminal apparatus 12 sending the prescription-related information. It should be noted that, instead of receiving a medicine name and a prescribed quantity from the first terminal apparatus 12, the controller 41 may recognize the medicine name and the prescribed quantity by determining the medicine name and the prescribed quantity based on the prescription-related information. It should be noted that, when the controller 41 determines the medicine name and the prescribed quantity, in a case in which the prescription-related information includes the identification information for the third terminal apparatus 14 and identification information for the prescription, the controller 41 receives the identified prescription from the identified third terminal apparatus 14.

When the controller 41 recognizes a medicine name and a prescribed quantity corresponding to the prescription-related information, the controller 41 reads, from the data store 40, an inventory of the business place associated with the identification information for the first terminal apparatus 12 and an inventory of the vendor vehicle 16 associated with the identification information for the first terminal apparatus 12. The controller 41 checks an inventory status for the medicine having the received medicine name in the inventory of the business place and the inventory of the vendor vehicle 16 that have been read. By using determination criteria that are changed based on the inventory status, the controller 41 determines whether the vendor vehicle 16 can reach a point on the travel route of the patient within the travel time period of the patient corresponding to prescription-related information as described later.

In a case in which the prescribed quantity of the medicine is stocked by the vendor vehicle 16, the controller 41 controls the communication interface 39 to send to the on-board apparatus 15 a request for notification of the location of the vendor vehicle 16. When the location of the vendor vehicle 16 is received from the on-board apparatus 15 in response to the request for the notification of the location, the controller 41 determines whether the vendor vehicle 16 is able to reach a point on the travel route from the location within the travel time period. In a case in which it is determined that the vendor vehicle 16 is able to reach a point on the travel route from the location within the travel time period, the controller 41 authorizes the vendor vehicle 16 to sell the medicine.

In a case in which the prescribed quantity of the medicine is stocked by the business place, the controller 41 submits a request for notification of the location of the vendor vehicle 16 and receives the location of the vendor vehicle 16 from the on-board apparatus 15. The controller 41 determines whether the vendor vehicle 16 is able to travel from the location of the vendor vehicle 16 via the business place and reach a point on the travel route within the travel time period. It should be noted that, in a case in which the vendor vehicle 16 travels via the business place, a time taken to load the medicine into the vendor vehicle 16 at the business place may be considered. In a case in which it is determined that the vendor vehicle 16 is able to travel from the location of the vendor vehicle 16 via the business place and reach a point on the travel route within the travel time period, the controller 41 authorizes the vendor vehicle 16 to sell the medicine.

In a case in which the medicine is not stocked in either the vendor vehicle 16 or the business place, the controller 41 controls the communication interface 39 to send a prescribing cancellation indication to the first terminal apparatus 12 of identification information associated with the vendor vehicle 16 and the business place. Additionally, the controller 41 may, with respect to another first terminal apparatus 12 associated with another vendor vehicle 16 covering a moving area including at least part of the travel route, send the prescription-related information, check an inventory status, and determine, in accordance with the inventory status, the possibility that the vendor vehicle 16 reach a point on the travel route.

When the controller 41 authorizes the vendor vehicle 16 to sell the medicine as described above, the controller 41 determines a location on the travel route as a parking location. The controller 41 also determines a collection time by which the vendor vehicle 16 is controlled to reach the parking location. The method of determining the parking location and the collection time is similar to the determination method implemented by the controller 22 of the first terminal apparatus 12. Instead of determining the parking location on the travel route and the collection time, the controller 41 may control the communication interface 39 to send the travel route and the travel time period to the first terminal apparatus 12 and then receive from the first terminal apparatus 12 the parking location and the collection time that are determined by the first terminal apparatus 12.

Additionally, the controller 41 generates authentication information for authenticating the legitimate patient for the medicine. The controller 41 controls the communication interface 39 to send the generated authentication information, the parking location, and the collection time to the on-board apparatus 15 and the second terminal apparatus 13. The controller 41 controls the communication interface 39 to also send the prescribed medicine name and the prescribed quantity to the on-board apparatus 15.

When at least one of a purchase history, an activity history, a medical examination history, a medication history, and an allergy record is received together with the travel route, the controller 41 generates an item suggestion based on the at least one of the purchase history, the activity history, the medical examination history, the medication history, and the allergy record. For example, in a case in which the frequency of purchasing a particular item in the travel time period is determined to be relatively high based on the purchase history, the controller 41 generates an item suggestion which suggests purchase of the particular item. Alternatively, for example, in a case in which the rate of purchasing a particular item is determined to be relatively high by performing machine learning in accordance with the purchase history stored in the data store 40, the controller 41 generates an item suggestion which suggests purchase of the particular item. The controller 41 controls the communication interface 39 to send the generated item suggestion together with the parking location, the collection time, and the authentication information to the on-board apparatus 15. Additionally, the controller 41 may control the communication interface 39 to send the generated item suggestion together with the parking location, the collection time, and the authentication information to the second terminal apparatus 13.

When a dispensing completion indication is received from the on-board apparatus 15, the controller 41 controls the communication interface 39 to send the dispensing completion indication to the first terminal apparatus 12 associated with the vendor vehicle 16. When a sales quantity is received from the on-board apparatus 15, the controller 41 updates the inventory of medicines stored in the data store 40 and controls the communication interface 39 to send the sales quantity to the first terminal apparatus 12 associated with the vendor vehicle 16. When a replenishment quantity of a medicine is received from the on-board apparatus 15, the controller 41 updates the inventory of medicines stored in the data store 40 and controls the communication interface 39 to send the replenishment quantity to the first terminal apparatus 12 associated with the vendor vehicle 16.

Figure 2:
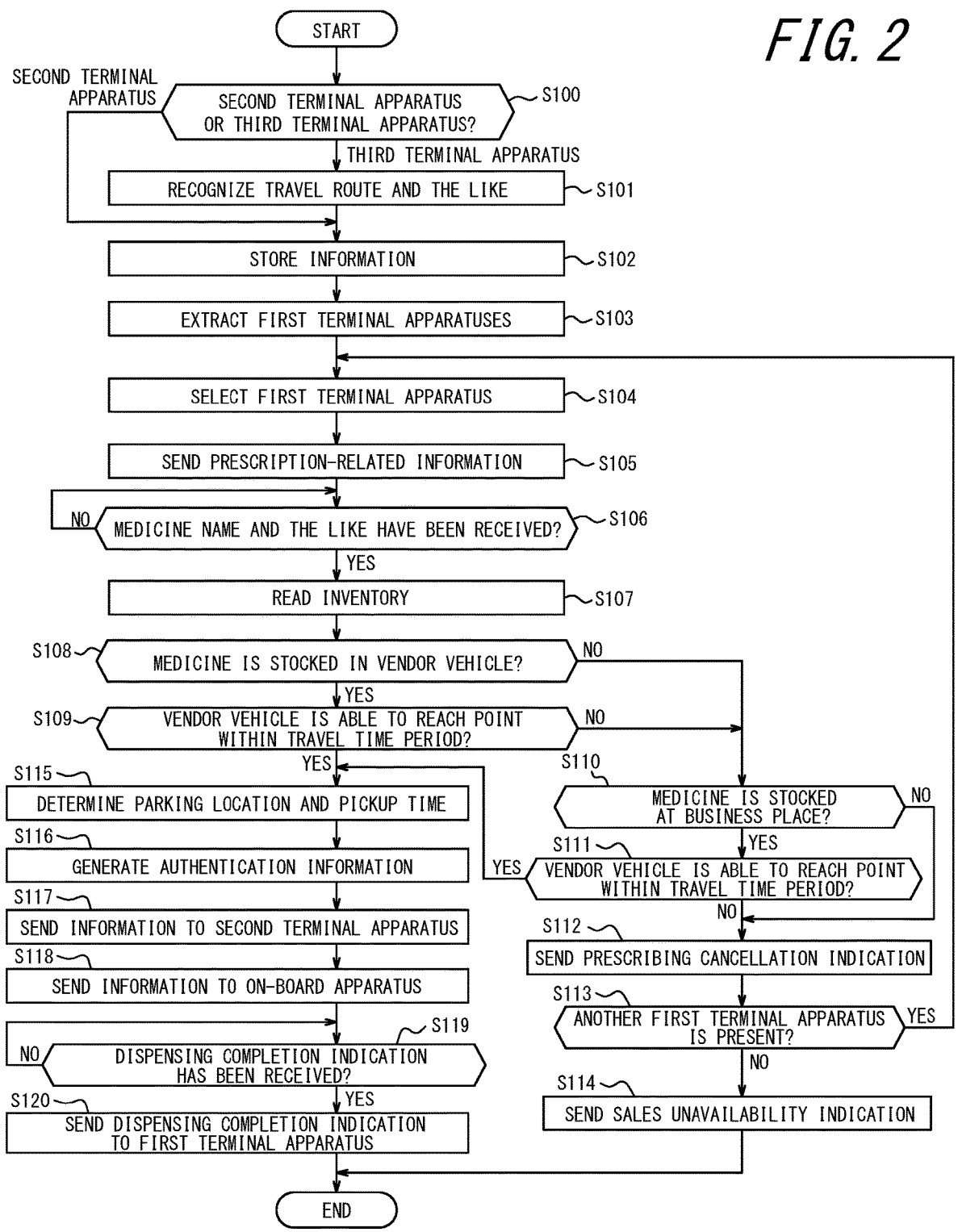
FIG. 2 is a flowchart of dispenser vehicle dispatch processing performed by a controller of the information processing apparatus in FIG. 1.

Next, dispenser vehicle dispatch processing performed by the controller 41 of the information processing apparatus 10 in the present embodiment is described with reference to a flowchart in FIG. 2. The dispenser vehicle dispatch processing is started when, for example, the communication interface 39 receives prescription-related information sent from the second terminal apparatus 13 or the third terminal apparatus 14.

In step S100, the controller 41 determines which of the second terminal apparatus 13 and the third terminal apparatus 14 sends the prescription-related information. In a case in which the second terminal apparatus 13 sends prescription-related information, the process proceeds to step S102. In a case in which the third terminal apparatus 14 sends prescription-related information, the process proceeds to step S101.

In step S101, the controller 41 recognizes a travel route and a travel time period of the owner of the second terminal apparatus 13 based on the identification information for the second terminal apparatus 13 received together with the prescription-related information. Additionally, based on the identification information for the second terminal apparatus 13 received together with the prescription-related information, the controller 41 requests the second terminal apparatus 13 or the server apparatus that monitors the activity history and the like of the second terminal apparatus 13 to send at least one of a purchase history, an activity history, a medical examination history, a medication history, and an allergy record and receives at least one of the purchase history, the activity history, the medical examination history, the medication history, and the allergy record. After the travel route and the travel time period are recognized, the process proceeds to step S102.

In step S102, the controller 41 stores in the data store 40 the prescription-related information and the identification information for the second terminal apparatus 13 determined to have been received in step S100, and the travel route, the travel time period, and the at least one of the purchase history, the activity history, the medical examination history, the medication history, and the allergy record determined to have been received with the prescription-related information in step S100. Alternatively, the controller 41 stores in the data store 40 the prescription-related information the identification information for the second terminal apparatus 13 received in step S101, and the travel route, the travel time period, and the at least one of the purchase history, the activity history, the medical examination history, the medication history, and the allergy record that are recognized in step S101. After the information is stored, the process proceeds to step S103.

In step S103, the controller 41 extracts the first terminal apparatus 12 associated with the vendor vehicle 16 in a moving area including at least part of the travel route stored in step S102. The controller 41 may extract a plurality of the first terminal apparatuses 12. After the first terminal apparatus 12 is extracted, the process proceeds to step S104.

In step S104, the controller 41 selects one first terminal apparatus 12 from the first terminal apparatuses 12 extracted in step S103. For example, the one first terminal apparatus 12 may be selected from the first terminal apparatuses 12 as selection targets based on, for example, a length by which the moving area of the vendor vehicle 16 and the travel route overlap. After the one first terminal apparatus 12 is selected, the process proceeds to step S105.

In step S105, the controller 41 controls the communication interface 39 to send the prescription-related information stored in step S102 to the first terminal apparatus 12 selected in step S104. After the prescription-related information is sent, the process proceeds to step S106.

In step S106, the controller 41 determines whether a medicine name and a prescribed quantity corresponding to the prescription-related information sent in step S105 have been received. In a case in which the medicine name and the prescribed quantity have not been received, the process returns to step S106. In a case in which the medicine name and the prescribed quantity have been received, the process proceeds to step S107. It should be noted that, in a case in which the configuration is made such that the medicine name and the prescribed quantity are determined based on prescription-related information, the controller 41 can determine a medicine name and a prescribed quantity instead of steps S105 and S106.

In step S107, the controller 41 reads, from the data store 40, the inventory of the medicine with the medicine name determined in step S106 to have been received. After the inventory is read, the process proceeds to step S108.

In step S108, the controller 41 determines, in accordance with the inventory of the medicine that is read in step S107, whether the medicine stocked by the vendor vehicle 16 is equal to or more than the prescribed quantity determined to have been received in step S106. In a case in which a sufficient quantity of the medicine is stocked by the vendor vehicle 16, the process proceeds to step S109. In a case in which a sufficient quantity of the medicine is not stocked by the vendor vehicle 16, the process proceeds to step S110.

In step S109, the controller 41 requests a notification of the location of the vendor vehicle 16 and in turn receives the location of the vendor vehicle 16. The controller 41 determines whether the vendor vehicle 16 is able to reach a point on the travel route stored in step S102 from the location of the vendor vehicle 16 within the travel time period. In a case in which the vendor vehicle 16 is not able to reach a point on the travel route, the process proceeds to step S110. In a case in which the vendor vehicle 16 is able to reach a point on the travel route, the process proceeds to step S115.

In step S110, the controller 41 determines, in accordance with the inventory of the medicine that is read in step S107, whether the medicine stocked by the business place is equal to or more than the prescribed quantity determined to have been received in step S106. In a case in which a sufficient quantity of the medicine is stocked by the business place, the process proceeds to step S111. In a case in which a sufficient quantity of the medicine is not stocked by the business place, the process proceeds to step S112.

In step S111, the controller 41 requests notification of the location of the vendor vehicle 16 and in turn receives the location of the vendor vehicle 16. The controller 41 determines whether the vendor vehicle 16 is able to reach a point on the travel route stored in step S102 from the location of the vendor vehicle 16 via the business place within the travel time period. In a case in which the vendor vehicle 16 is not able to reach a point on the travel route via the business place, the process proceeds to step S112. In a case in which the vendor vehicle 16 is able to reach a point on the travel route via the business place, the process proceeds to step S115.

In step S112, the controller 41 controls the communication interface 39 to send a prescription cancellation indication to the first terminal apparatus 12 selected in step S104. The controller 41 excludes the first terminal apparatus 12 from the selection targets. After the prescription cancellation indication is sent, the process proceeds to step S113.

In step S113, the controller 41 determines whether another first terminal apparatus 12 exists as a selection target. In a case in which another first terminal apparatus 12 exists as a selection target, the process returns to step S104. In a case in which another first terminal apparatus 12 does not exist as a selection target, the process proceeds to step S114.

In step S114, the controller 41 controls the communication interface 39 to send a sales unavailability indication, which indicates that dispensing of the medicine by a vendor vehicle 16 is not possible, to the second terminal apparatus 13 for the identification information stored in step S102. After the sales unavailability indication is sent, the dispenser vehicle dispatch processing is ended.

In step S115, the controller 41 determines a location on the travel route stored in step S102 as a parking location. The controller 41 also determines a collection time by which the vendor vehicle 16 is controlled to reach the parking location. After the location and the collection time are determined, the process proceeds to step S116. It should be noted that, for a configuration in which the first terminal apparatus 12 is asked for a parking location and a collection time, the controller 41 may ask the first terminal apparatus 12 for a parking location and a collection time and receive a parking location and a collection time in step S115.

In step S116, the controller 41 generates authentication information. After the authentication information is generated, the process proceeds to step S117.

In step S117, the controller 41 controls the communication interface 39 to send the parking location and the collection time determined in step S115 and the authentication information generated in step S116 to the second terminal apparatus 13 for the identification information stored in step S102. After the information is sent, the process proceeds to step S118.

In step S118, the controller 41 controls the communication interface 39 to send, to the on-board apparatus 15 of the vendor vehicle 16 associated with the first terminal apparatus 12 selected in step S104, the parking location and the collection time determined in step S115, the authentication information generated in step S116, the medicine name and the prescribed quantity determined to have been received in step S106, and the at least one of the purchase history, the activity history, the medical examination history, the medication history, and the allergy record stored in step S102. After the information is sent, the process proceeds to step S119.

In step S119, the controller 41 determines whether the communication interface 39 has received a dispensing completion indication from the on-board apparatus 15. In a case in which a dispensing completion indication has not been received, the process returns to step S119. In a case in which a dispensing completion indication has been received, the process proceeds to step S120.

In step S120, the controller 41 controls the communication interface 39 to send, to the first terminal apparatus 12 selected in step S104, the dispensing completion indication determined to have been received in step S119. After dispensing completion indication is sent, the dispenser vehicle dispatch processing is ended.

The information processing apparatus 10 according to the present embodiment configured as described above sends at least one location on a travel route to the on-board apparatus 15 covering a moving area including at least part of the travel route when prescription-related information is received. With this configuration, the information processing apparatus 10 can cause the vendor vehicle 16, into which medicines are loaded, to recognize a patient who desires to purchase medicines. Thus, the information processing apparatus 10 can increase the opportunity for the vendor vehicle 16 to sell medicines. According to this, the information processing apparatus 10 can decrease the need for patients to visit pharmacies because the vendor vehicle 16 moves to travel routes along which patients are due to travel. As a result, the information processing apparatus 10 can reduce effort required by patients to receive the medicines.

Furthermore, the information processing apparatus 10 according to the present embodiment sends, to the second terminal apparatus 13, a parking location at which the vendor vehicle 16 is to park on the travel route. With this configuration, the information processing apparatus 10 can cause the patient as the owner of the second terminal apparatus 13 to recognize the parking location that serves as a location at which the medicine is to be collected. As a result, the information processing apparatus 10 can increase the possibility that the patient can come into contact with the vendor vehicle 16, and thus, it is possible to improve the certainty of dispensing medicines.

Further, the information processing apparatus 10 according to the present embodiment sends authentication information together with the parking location to the on-board apparatus 15 and the second terminal apparatus 13. With this configuration, the information processing apparatus 10 improves the certainty of dispensing a medicine from the vendor vehicle 16 using the on-board apparatus 15 to a patient having a right to be provided with the medicine in accordance with a prescription. Thus, the information processing apparatus 10 reduces the possibility of incorrectly dispensing medicines in accordance with prescriptions.

Moreover, the information processing apparatus 10 according to the present embodiment sends a medicine name corresponding to prescription-related information to the on-board apparatus 15. With this configuration, the information processing apparatus 10 can prepare medicines before patients come into contact with the vendor vehicle 16. Thus, the information processing apparatus 10 can shorten waiting times for preparing medicines, such that the information processing apparatus 10 can further reduce the effort required by patients to receive the medicines.

Furthermore, by using determination criteria that are changed based on an inventory status of medicines in the vendor vehicle 16 and the business place of the supplier, the information processing apparatus 10 according to the present embodiment determines whether the vendor vehicle 16 is able to reach a point on the travel route within the travel time period and, in a case in which the vendor vehicle 16 is able to reach a point on the travel route within the travel time period, the information processing apparatus 10 sends, to the on-board apparatus 15, at least one location on the travel route. With this configuration, the information processing apparatus 10 can avoid unnecessary travelling of the vendor vehicle 16 to a travel route without sufficient medicines in stock.

Further, the information processing apparatus 10 according to the present embodiment sends prescription-related information to the first terminal apparatus 12 and receives a medicine name from the first terminal apparatus 12. With this configuration, the information processing apparatus 10 can cause an operator of the first terminal apparatus 12 to prescribe medicines. Thus, even in a case in which qualified people such as pharmacists are permitted by laws or the like to prescribe medicines in accordance with prescriptions, the information processing apparatus 10 can legally prescribe medicines.

Moreover, the information processing apparatus 10 according to the present embodiment determines a medicine based on prescription-related information. With this configuration, the information processing apparatus 10 can prescribe a medicine without human decision. Thus, in a case in which there is no law restricting the prescribing of medicines to qualified people, the information processing apparatus 10 can reduce the effort for prescribing of medicines.

Furthermore, the information processing apparatus 10 according to the present embodiment sends, to the first terminal apparatus 12 or the on-board apparatus 15, an item suggestion based on at least one of a purchase history, an activity history, a medical examination history, a medication history, an allergy record, and a travel route of the patient. With this configuration, the information processing apparatus 10 can increase the opportunity for the vendor vehicle 16 to sell items other than medicines.

While the present disclosure has been described with reference to the accompanying drawings and the examples, it should be noted that various changes and modifications based on the present disclosure may be easily made by those skilled in the art. It should be noted that these changes and modifications are therefore embraced in the scope of the present disclosure. For example, the functions and the like included in the constituents and steps may be rearranged in a logically consistent manner, and a plurality of means or steps may be combined together or divided.

For example, some of the processing operations performed by the information processing apparatus 10, the first terminal apparatus 12, the second terminal apparatus 13, the third terminal apparatus 14, or the on-board apparatus 15 in the embodiment described above may be carried out by another apparatus.

In particular, some of the processing operations performed by the information processing apparatus 10 may be carried out by the first terminal apparatus 12. For example, the first terminal apparatus 12 may receive a travel route from the information processing apparatus 10 having received prescription-related information, determine, based on the travel route, a parking position at which the vendor vehicle 16 covering a moving area including at least part of the travel route is to be parked, and send the determined parking position to the on-board apparatus 15 using the vendor vehicle 16.

Further, for example, the first terminal apparatus 12 may receive prescription-related information from the information processing apparatus 10; the first terminal apparatus 12 may output a request for user input of a medicine and a prescribed quantity corresponding to the prescription-related information; the first terminal apparatus 12 may detect user inputs of a medicine and a prescribed quantity; by using determination criteria that are changed in accordance with an inventory status of medicines in the vendor vehicle 16 and the business place of the supplier managing the vendor vehicle 16, the first terminal apparatus 12 may determine whether the vendor vehicle 16 is able to reach a point on a travel route within a travel time period in which the travel route is to be travelled; in a case in which the vendor vehicle 16 is able to reach a point on the travel route within the travel time period, the first terminal apparatus 12 may send a parking position to the on-board apparatus 15 which uses the vendor vehicle 16. In this configuration, the information processing apparatus 10 may send to the first terminal apparatus 12 prescription-related information together with a travel route.

Furthermore, for example, a general electronic device such as a smartphone or a computer may be configured to function as the information processing apparatus 10, the first terminal apparatus 12, the second terminal apparatus 13, the third terminal apparatus 14, or the on-board apparatus 15 according to the embodiment described above. Specifically, a program in which details of processing for implementing the functions of, for example, the information processing apparatus 10 according to the embodiment are stored in a memory of an electronic device, and a processor of the electronic device reads and runs the program. Thus, the disclosure according to the present embodiment may be implemented as a program that can be run by a processor. The program may be downloaded through the network 17, or the program may be stored in a portable non-transitory recording/storage medium readable by electronic devices and the program may be read from the medium by an electronic device.

Moreover, while in the information processing system 11 the first terminal apparatus 12 and the on-board apparatus 15 are provided separately, for example, all the functions of the first terminal apparatus 12 described above may be performed by the on-board apparatus 15. For example, in a case in which the only the business place of a mobile retail service provider is the vendor vehicle 16, communication may be established among the information processing apparatus 10 and the third terminal apparatus 14, and the first terminal apparatus 12 in the embodiment described above, together with the on-board apparatus 15.

The invention claimed is:

1. An information processing apparatus comprising:
   a data store configured to:
      store an inventory of medicines in a vendor vehicle covering a moving area that includes at least part of a travel route along which a patient is expected to travel; and
      store an inventory of medicines in a business place of a supplier managing the vendor vehicle; and
   a controller configured to:
      upon receipt of prescription-related information on the patient, read the inventory of medicines in the vendor vehicle, from the data store, to check whether a prescribed quantity of a medicine corresponding to the prescription-related information is stocked in the vendor vehicle;
      upon confirmation that the prescribed quantity of the medicine corresponding to the prescription-related information is stocked in the vendor vehicle, determine whether the vendor vehicle is able to reach a point on the travel route within a travel time period in which the patient is expected to travel along the travel route;
      upon confirmation that the prescribed quantity of the medicine corresponding to the prescription-related information is not stocked in the vendor vehicle, read the inventory of medicines in the business place, from the data store, to check whether the prescribed quantity of the medicine corresponding to the prescription-related information is stocked in the business place;
      upon confirmation that the prescribed quantity of the medicine corresponding to the prescription-related information is stocked in the business place, determine whether the vendor vehicle is able to reach a point on the travel route within the travel time period via the business place; and
      upon determination that the vendor vehicle is able to reach a point on the travel route within the travel time period, send, to an on-board apparatus for the vendor vehicle, at least one location on the travel route.

2. The information processing apparatus according to claim 1, wherein
   the controller is configured to receive the travel route together with the prescription-related information from a second terminal apparatus owned by the patient.

3. The information processing apparatus according to claim 1, wherein the controller is configured to:
   receive the prescription-related information together with identification information for identifying a second terminal apparatus owned by the patient;
   determine a departure point and a destination point of travel by the patient based on an activity history of the second terminal apparatus determined by using the identification information; and estimate the travel route based on the determined departure point and the determined destination point.

4. The information processing apparatus according to claim 1, wherein
the at least one location on the travel route sent to the on-board apparatus for the vendor vehicle includes a parking location at which the vendor vehicle is to park on the travel route.

5. The information processing apparatus according to claim 4, wherein
the controller is configured to determine the parking location based on the travel route.

6. The information processing apparatus according to claim 4, wherein
the controller is configured to send the travel route to a first terminal apparatus associated with the supplier and receive the parking location from the first terminal apparatus.

7. The information processing apparatus according to claim 4, wherein
the controller is configured to send the parking location to a second terminal apparatus owned by the patient.

8. The information processing apparatus according to claim 7, wherein
the controller is configured to send authentication information together with the parking location to the on-board apparatus for the vendor vehicle and the second terminal apparatus.

9. The information processing apparatus according to claim 1, wherein
the controller is configured to send, to the on-board apparatus for the vendor vehicle, a medicine name corresponding to the prescription-related information together with the at least one location on the travel route.

10. The information processing apparatus according to claim 9, wherein
the controller is configured to send the prescription-related information to a first terminal apparatus associated with the supplier and receive the medicine name from the first terminal apparatus.

11. The information processing apparatus according to claim 9, wherein
the controller is configured to determine the medicine name based on the prescription-related information.

12. The information processing apparatus according to claim 1, wherein
the controller is configured to send, to a first terminal apparatus associated with the supplier or the on-board apparatus for the vendor vehicle, an item suggestion based on at least one of a purchase history, an activity history, a medical examination history, a medication history, and an allergy record of the patient.

13. An information processing system comprising:
the information processing apparatus according to claim 1; and
the on-board apparatus for the vendor vehicle, the on-board apparatus being configured to communicate with the information processing apparatus.

14. An information processing method implemented by an information processing apparatus configured to store an inventory of medicines in a vendor vehicle covering a moving area that includes at least part of a travel route along which a patient is expected to travel and an inventory of medicines in a business place of a supplier managing the vendor vehicle, the information processing method comprising:
upon receipt of prescription-related information on the patient reading the inventory of medicines in the vendor vehicle to check whether a prescribed quantity of a medicine corresponding to the prescription-related information is stocked in the vendor vehicle;
upon confirmation that the prescribed quantity of the medicine corresponding to the prescription-related information is stocked in the vendor vehicle, determining whether the vendor vehicle is able to reach a point on the travel route within a travel time period in which the patient is expected to travel along the travel route;
upon confirmation that the prescribed quantity of the medicine corresponding to the prescription-related information is not stocked in the vendor vehicle, reading the inventory of medicines in the business place to check whether the prescribed quantity of the medicine corresponding to the prescription-related information is stocked in the business place;
upon confirmation that the prescribed quantity of the medicine corresponding to the prescription-related information is stocked in the business place, determining whether the vendor vehicle is able to reach a point on the travel route within the travel time period via the business place; and
upon determination that the vendor vehicle is able to reach a point on the travel route within the travel time period, sending, to an on-board apparatus for the vendor vehicle, at least one location on the travel route.

15. The information processing method according to claim 14, further comprising:
sending, to a first terminal apparatus associated with the supplier or the on-board apparatus for the vendor vehicle, an item suggestion based on at least one of a purchase history, an activity history, a medical examination history, a medication history, and an allergy record of the patient.

16. The information processing method according to claim 14, further comprising:
receiving the prescription-related information together with identification information for identifying a second terminal apparatus owned by the patient;
determining a departure point and a destination point of travel by the patient based on an activity history of the second terminal apparatus determined by using the identification information; and
estimating the travel route based on the determined departure point and the determined destination point.

* * * * *